United States Patent [19]

Greven et al.

[11] 4,104,371
[45] Aug. 1, 1978

[54] PSYCHOPHARMACOLOGICALLY ACTIVE PEPTIDES AND PEPTIDE-DERIVATIVES, AND THE USE THEREOF

[75] Inventors: Hendrik Marie Greven, Heesch; David de Wied, Bilthoven, both of Netherlands

[73] Assignee: Akzona Incorporated, Asheville, N.C.

[21] Appl. No.: 811,859

[22] Filed: Jun. 30, 1977

[30] Foreign Application Priority Data

Jul. 12, 1976 [NL] Netherlands ............... 7607684

[51] Int. Cl.² ............... A61K 37/100; C07C 103/52
[52] U.S. Cl. ............... 424/177; 260/112.5 R
[58] Field of Search ............... 260/112.5 R; 424/177

[56] References Cited
U.S. PATENT DOCUMENTS

| | | | |
|---|---|---|---|
| 3,842,064 | 10/1974 | Greven et al. | 260/112.5 |
| 3,853,836 | 12/1974 | Greven | 260/112.5 |
| 3,853,838 | 12/1974 | Greven | 260/112.5 |
| 3,856,770 | 12/1974 | Greven | 260/112.5 |

*Primary Examiner*—Delbert R. Phillips
*Assistant Examiner*—Blondel Hazel

*Attorney, Agent, or Firm*—Robert H. Falk; Charles A. Wendel; Francis W. Young

[57] ABSTRACT

Biologically active novel peptides and peptide-derivatives of the general formula:

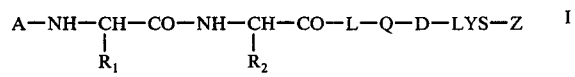

where
A represents H-(L or D)Met, H-(L or D)Met(→O), H-(L or D)Met(→O$_2$) desamino-Met, desamino-Met(→O), desamino-Met(→O$_2$) or the group H$_2$N—B—CO—;
B represents a branched or straight-chain alkylene (C$_1$-C$_6$) or alkylidene (C$_1$-C$_6$) group;
Q represents the amino-acid residue —NH—CHR—CO—;
R represents alkyl (C$_1$-C$_6$), p-hydroxyphenylmethyl, 3-indolylmethyl or phenylmethyl;
R$_1$ and R$_2$ represent hydrogen or an alkyl(1–6C) group, and
Z represents N-(phenylalkyl)amino, N-(β-indolylalkyl)amino, L-Trp-OH, L-Phe-OH, L-Trp-Gly-OH or L-Phe-Gly-OH, as well as the functional derivatives thereof.

23 Claims, No Drawings

PSYCHOPHARMACOLOGICALLY ACTIVE PEPTIDES AND PEPTIDE-DERIVATIVES, AND THE USE THEREOF

BACKGROUND OF THE INVENTION

1. Field of the Invention

The peptides and peptide derivatives herein referred to possess valuable psychopharmacological properties. In particular, they inhibit the extinction of the conditioned flight response, as a result of which they are eminently suitable for the treatment of certain mental disorders in which stimulation of brain function is desirable, such as for senility or other old-age infirmites.

2. Description of the Prior Art

From Eur. J. Pharmacol. 2, 14 (1967) it is known, that certain peptide fragments of the natural adrenocorticotrophic hormones (ACTH) retard the extinction of the conditioned flight response. Specifically, the peptide consisting of the aminoacid sequence 4–10 of ACTH proved to be the smallest peptide fragment active in this respect.

In addition to the psychopharmacological properties noted, the peptide with the amino-acid sequence 4–10 ACTH also possesses slight MSH activity, as is usual with this type of ACTH-fragments. Although the effect of a low dosage of a peptide with MSH activity is still not fully known, a search has nevertheless been made for peptides with at least the same psychopharmacological activity but with no, or much reduced, MSH activity.

In the U.S. Pat. No. 3,853,836 it is revealed that the amino-acid sequence 4–10 ACTH is not essential for psychopharmacological activity, and that this activity is attributable to a much shorter peptide, namely 4–6 ATCH. It furthermore appears that the N-terminal amino-acid L-Met may, without loss of activity, be replaced by D-Met, L- or D-Met(→C), L- or D-Met(→O$_2$), desamino-Met, desamino-Met(→O) or desamino-Met(→O$_2$), or by the group

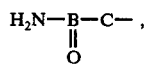

in which B represents a branched or straight chain alkylene group with 1–6 carbon atoms.

In the U.S. Pat. No. 3,856,770 it is furthermore reported that replacement of the C-terminal peptide residue —L—Trp—Gly—OH in the original 4–10 ACTH peptide by one of the groups —L—Phe—OH, L-Phe-Gly-OH, a phenylalkylamino group or a (3-indolyl)alkyl-amino group results in an increase of the psychopharmacological activity.

In the U.S. Pat. No. 3,842,064 it is furthermore reported that a considerable increase of the psychopharmacological activity is obtained by replacing L-arginine in the original 4–10 ACTH peptide, or in one of the modified peptides described in the above-noted patent specifications, by D-lysine.

In this latter paptent specification, the most active peptides are described, namely those peptides conforming to the general formula:

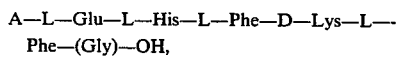

where A has the meaning noted above. These peptides prove to possess an activity which is approximately 1000x stronger than rhat of the original 4–10 ACTH.

SUMMARY OF THE INVENTION

Surprisingly, it has now been found that the amino-acid residues Glu and His, until now considered essential for activity, may be replaced without any loss of activity by lower aliphatic amino-acid residues such as Ala, Leu, Val and Ile, which may be utilized far more simply and cheaply than Glu and His in the peptide synthesis.

It has also been verified that the amino-acid L-Phe in position 7 of the original 4–10 ACTH could be replaced by other laevo-rotary amino-acids, including the lower aliphatic amino-acids named above.

The invention therefore relates to peptides and peptide-derivatives of the general formula:

$$\text{A—NH—CHR}_1\text{—CO—NH—CHR}_2\text{—CO—L—Q—D—Lys—Z} \quad \text{I}$$

where
A represents H—(L or D)Met, H—(L or D)Met(→O), H—(L or D)Met(→O$_2$),
  desamino-Met, desamino-Met(→O), desamino-Met(→O$_2$),
or the group H$_2$N—B—CO—;
B represents a branched or straight chain alkylene (C$_1$-C$_6$) or alkylidene (C$_1$-C$_6$) group,
Q represents the amino-acid residue —NH—CHR—CO—;
R represents alkyl (C$_1$-C$_6$), p-hydroxyphenylmethyl, 3-indolylmethyl or phenylmethyl;
R$_1$ and R$_2$ represent hydrogen or an alkyl (1-6C) group; and
Z represents N-(phenylalkyl)amino, N-(β-indolylalkyl)-amino, L—Trp—OH, L—Phe—OH, L—Trp—Gly—OH or L—Phe—Gly—OH, as well as the functional derivatives thereof and to the use of these compounds in a pharmacetical formulation.

The groups named as terminal groups in the definition of Z, namely N(phenylalkyl)-amino and N(β-indolylalkyl)amino, are groups which differ in the main from the related amino-acid residues by the absence of the carboxyl group.

By N(phenylalkyl)amino or as the case may be N(β-indolylalkyl)amino groups are understood the groups

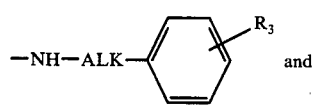

and

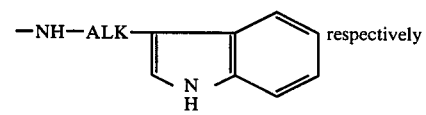 respectively where Alk represents an alkylene group of 1–6 C, and preferably ethyl and R$_3$ represents hydrogen, halogen, hydroxy, an alkyl group with 1-4 carbon atoms or an alkoxy group with 1-4 carbon atoms.

DESCRIPTION OF THE PREFERRED EMBODIMENTS

The peptides and peptide derivatives according to the general formula I are prepared in ways usual for such compounds. The most frequently used methods for the preparation of the peptides herein referred to may be summarized as follows:

(a) condensation in the presence of a condensation agent of a compound (amino-acid, peptide) containing a free carboxyl group, and in which other reactive groups have been protected, with a compound (amino-acid, peptide or amine) containing a free amino group and in which other reactive groups have likewise been protected, (b) condensation of a compound (amino-acid, peptide) containing an activated carboxyl group, in which other reactive groups have optionally been protected, with a compound (amino-acid, peptide, amine) containing a free amino group and in which other reactive groups have been protected, after which the protecting groups, if desired, may be removed.

Methods of activating the carboxyl group include the conversion of this group into an acid halide, an azide, anhydride, imidazolide or an activated ester such as the N-hydroxy-succinimide ester or the p-nitrophenyl ester.

The amino-group may be activated by conversion of this group into a phosphite amide or by use of the "phosphorazo" method.

The most usual methods for the above-noted condensation reactions are: the carbodi-imide method, the azide method, the mixed anhydride method and the activated ester method, as described in "The Peptides", volume I, 1965 (Academic Press), E. Schroeder and K. Lubke. The so-called "Solid Phase" method of Merrifield, described in J. Am. Chem. Soc. 85, 2149 (1963) may furthermore be used for the preparation of the peptides or peptide derivatives according to the invention.

The reaction groups which must be prevented from participation in the condensation reaction are effectively protected by so-called protecting groups which can easily be removed again, for example by hydrolysis or reduction. For example, a carboxyl group may be effectively protected by esterification with methanol, ethanol, tertiary butanol, benzyl alcohol or p-nitrobenzyl alcohol, or by conversion into an amide. This latter protecting group is however very difficult to remove, so that it is recommendable that this group is only used to protect the carboxyl group of the C-terminal amino-acid in the final peptide.

In this case, the peptide synthesis leads directly to the amide of the peptides according to formula I.

Groups which can effectively protect an amino acid group are usually acid groups, for example an acid group derived from an aliphatic, aromatic, araliphatic or heterocyclic carboxylic acid, such as acetyl, benzoyl or a pyridine-carboxyl group, or an acid group derived from carbonic acid, such as the ethoxycarbonyl, benzyloxycarbonyl, t-butyloxycarbonyl or p-methoxybenzyloxycarbonyl group, or a group derived from a sulphonic acid, such as the benzene-sulphonyl or p-toluene-sulphonyl group, but others groups, such as substituted or unsubstituted aryl or aralkyl groups, for example the benzyl and triphenylmethyl groups, or groups such as the o-nitrophenylsulphenyl and 2-benzoyl-1-methylvinyl groups, may also be used.

It is often recommendable that the $\epsilon$-amino group os lysine and optionally the phenolic hydroxyl group of tyrosine are also protected. This latter protection is however not always essential. Usual protecting groups in this connexion are a tertiry-butyloxycarbonyl or a tosyl group for the $\epsilon$-amino group of lysine, and a benzyl group for the phenolic hydroxyl group of tyrosine.

The protecting groups may be cleaved by various conventional methods, depending on the nature of the group concerned, for example with the aid of trifluoroacetic acid or by mild reduction, for example with hydrogen and a catalyst, such as palladium, or with HBr in glacial acetic acid.

Peptides according to the present invention having (l or D) Met($\rightarrow$C) or desamino-Met($\rightarrow$O) as the N-terminal residue may be prepared from the corresponding Met or desamino-Met peptide my mild oxidation in a known way, for example with dilute hydrogen peroxide or a peracid. Such an oxidation results in a mixture of the S- and R-sulphoxides, which can be resolved to give the separate diastero-isomers in a way known in itself, for example by selective crystallization. The separate diastereo-isomers may also be obtained directly by coupling (L or D)-methionine-S(or R—)-sulphoxide, or the corresponding desamino-derivative thereof, with the remainder of the peptide fragment.

The peptides according to the present invention, having (L or D)—Met($\rightarrow O_2$) or desamino-Met($\rightarrow O_2$) as N—terminal residue, can be obtained by oxidation of the (desamino)Met-peptide I or by coupling (desamino)-Met-sulphone with the remainder of the peptide fragment.

By functional derivatives of the peptides according to general formula I are understood:

1. Acid addition salts or metal salts, preferably alkali metal salts, such as the sodium salts;
2. Peptides according to general formula I, where one or more free amino groups have been substituted by an acyl group, derived from an aliphatic carboxylic acid with 1-6 carbon atoms, e.g. acetyl, propionyl, butyryl, etc.
3. Amides, optionally alkyl-substituted, of the present peptides, such as the unsubstituted amides or mono- or di-alkyl(1-6C) amides, e.g. the mono-or dimethyl amides
4. Esters of the present peptides, derived from aliphatic or araliphatic alcohols of 1-18 C atoms,
5. Metal complexes, formed by bringing peptides herein referred to into contact with a sparingly soluble salt, hydroxide or oxide of a metal, preferably zinc.

The acid addition salts are obtained by reaction of the peptides herein referred to with a pharmaceutically acceptable acid such as a hydrogen halide, phosphoric acid, acetic acid, maleic acid, tartaric acid or citric acid.

The peptides according to the invention and the derivatives defined above may be administered both orally and parenterally. The peptides are preferably used as injection preparations, for which purpose they are dissolved, suspended or emulsified in a suitable liquid medium. When mixed with suitable excipients or fillers, they may also be processed to give a form suitable for oral administration, such as pills, tablets or dragees. The peptides herein referred to may also be adinistered in the form of a suppository or a spray.

The peptides or peptide derivatives according to the invention are preferably used parenterally in a daily dosage of from 0,01 μg to 1 mg and orally in a daily dosage of from 0,1 mg to 50 mg per kg body weight, dependent upon the peptide's activity level.

Particularly valuable prepartions are obtained when the present peptides are processed to give a form in which the activity is prolonged. The metal complexes of the peptides are specifically meant in this context. These metal complexes can be obtained by bringing the peptides into contact with sparingly soluble metal salts, metal hydroxides or metal oxides. The metl phosphates, metal pyrophosphates and metal polyphosphates are generally used as sparingly soluble metal salts.

Metals which may be used in this process are the metals belonging to the transition elements, for example cobalt, nickel, copper, iron and preferably zinc, as well as metals belonging to the main groups of the periodic system and which are able to form complexes, such as magnesium and aluminium. The preparation of these metal complexes takes place in the usual way.

A metal complex complex may, for example, be obtained by adding the peptide and a sparingly soluble metal salt, metal hydroxide or metal oxide to an aqueous medium. The metal complex may also bo obtained by adding an alkaline medium to an aqueous solution of the peptide and a soluble metal salt, as a result of which the insoluble peptide-metal hydroxide complex is formed.

The metal complex may furthermore be obtained by adding the peptide, a soluble metal salt and a further soluble salt to an aqueous, preferably alkaline medium, resulting in the in situ formation of an insoluble peptide-metal salt complex.

The metal complexes may be immediately used as suspensions, or may, for example, be freeze-dried and later resuspended.

The definition of A includes the residues Met, desamino-Met, the corresponding sufloxide and sulfone of Met and desamino-Met, but also the amino-acid residue $H_2N—B—CO$, in which B is a branched or unbranched alkylene or alkylidene moiety with 1 to 6 carbon atoms, and preferably with 1 to 5 carbon atoms. The latter amino-acid residue preferably includes the natural α-amino-acid residues Gly, Ala, Val, Leu and Ile, but may also include other residues such as β-Ala or (α-Me)Ala.

The amino-acid residues $HN—CHR_1—CO$ and $HN—CHR_2—CO$ in the peptides according to the invention represent the same or different aliphatic α-amino-acid residues. Preferred aminoacid residues in this context are those, in which $R_1$ and $R_2$ represent hydrogen or alkyl (1-4 C) and especially the natural amino-acid residues Gly, Val, Leu, Ile and especially Ala.

The α-amino residue Q, defined as HN—CHR—CO, in the peptides of the invention preferably encompasses the natural amino acids Ala, Val, Leu, Ile, Tyr, Trp and Phe. The aminoacid residues, Phe, Leu and those residues, in which R represents a lower alkyl group (1-4 C), especially Ala (R =$CH_3$) are preferred.

Esters of the peptides of the invention are preferably derived from alkanols of from 1 to 8 carbon atoms, and especially from 1 o 4 carbon atoms, such as methanol, ethanol, propanol and butanol and may be prepared by esterification of the final peptide or by esterification of the starting amino acid in question whereby the ester moiety may serve as protecting group during the peptide-synthesis.

Amides are prepared in a similar way either by aminolysis of the final ester or by starting the peptide-synthesis from the amide of the amino acid in question.

Peptides according to the general formula I which are preferred are those peptides in which $R_1$ and $R_2$ represent identical groups, for example methyl (resulting in the amino-acid residue Ala), isopropyl (resulting in the amino-acid residue Val), or 2-methylpropyl (resulting in the amino-acid residue Leu).

"A" in the general formula I is preferably L-Met or desamino-Met, or the sulphoxides or sulphones derived from these two acid residues.

The symbol "Q" in the general formula I preferably represents one of the amino-acid residues L—Phe or L—Ala.

The symbol "Z" in the general formula I is preferably the amino-acid residue L—Phe—O or optionally the peptide residue L—Phe—Gly—OH, although this latter option represents an increase in chain length without any further increase in acitivity.

In the context of the invention herein referred to, the following peptides are particularly preferred:

H—L—Met—L—Ala—L—Ala—L—Phe—D—Lys—Phe—OH
H—L—Met(O)—L—Ala—L—Ala—L—Phe—D—Lys—L—Phe—OH
H—L—Met($O_2$)—L—Ala—L—Ala—L—Phe—D—Lys—L—Phe—OH
H—Met—L—Ala—L—Ala—L—Ala—L—Ala—D—Lys—L—Phe—Gly—OH
H—L—Met(O)—L—Ala—L—Ala—L—Ala—D—Lys—L—Phe—Gly—OH,
H—L—Met($O_2$)—L—Ala—L—Ala—Ala—L—Ala—D—Lys—L—Phe—OH,
desamino-Met—L—Ala—L—Ala—L—Phe—D—Lys—L—Phe—OH,
desamino-Met($O_2$)—L—Ala—L—Ala—L—Phe—D—Lys—L—Phe—OH,
desamino-Met(O)—Ala—L—Ala—L—Phe—D—Lys—L—Phe—Gly—OH, The observations below are made with respect to the examples which follow.

I. If no optical configuration is given, the L-form is inteneded.

II. The following abbreviations have been assigned to the protecting and activating groups used:
Boc = tertiary-butyloxycarbonyl
tBu = tertiary butyl
Me = methyl
ONP = p-nitrophenyloxy
Bzl = benzyl
ONB = nitrobenzyloxy
OSu = succinimido-N-oxy
Z = benzyloxycarbonyl.

III. The following abbreviations have been assigned to the solvents or reagents used:
Bz = benzene
To = toluene
EtOH = ethanol
Bu = butanol
Py = pyridine
Ac = acetic acid
EtOAc = ethyl-acetate
Fo = formic acid
Am = amyl alcohol
iPro = isopropanol
DMF = dimethylformamide
THF = tetrahydrofuran
DCCI = dicyclohexylcarbodi-imide DCHU = dicyclohexylurea
TAA = tri-ethylamine
TFA = trifluoro-acetic acid
Wa = water
NEM = N-ethylmorpholine
HOBt = N-hydroxybenztriazole IV. The following abbreviations have been used for the aminoacid groups:

Met = methionyl
Met(→O) = sulphoxide of methionyl
Met(→$O_2$) = sulphone of methionyl
Phe = phenylalanyl
Tyr = tyrosyl
Lys = lysyl
Trp = tryptophyl
Gly = glycyl
Val = valyl
Leu = leucyl
Ala = alanyl
Ile = isoleucyl
β-Ala = β-alanyl
(α-Me)Ala = α-methylalanyl.

V. The following abbreviations have been used for groups related to amino-acid residues:

| | |
|---|---|
| PPA | = N-(3-phenylpropyl)amino |
| PEA | = N-(2-phenylethyl)amino |
| HPEA | = N-(p-hydroxyphenylethyl)amino |
| Amf | = N-(2-phenylisopropyl)amino, derived from amphetamine |
| Tra | = N-(β-indolylethyl)amino, derived from tryptamine |
| Desamino-Met | = desamino-methionyl |
| Desamino-Met(→O) | = sulphoxide of desamino-methionyl (or 4-methylsulphinylbutyryl) |
| Desamino-Met(→$O_2$) | = sulphone of desamino-methionyl (or 4-methylsulphonylbutyryl). |

Preparation of starting materials

I. N-terminal part

1. Boc—Met—Ala—Ala—$N_2H_3$ (a). Boc—Ala—Ala—OMe: 20.79G Boc—Ala—OH is dissolved in 150ml DMF. After cooling to −10 ° C, 15.84ml TAA is added, followed by 10.45ml ethyl chloroformate. The whole is stirred for 10 minutes at −10° C, after which a solution of 13.9g H—Ala—OMe.HCl in 150ml DMF and 14.4ml TAA is added to the reaction mixture and the whole is stirred for a further 15 minutes at −10° C, for 2 hours at 0° C and finally for 8 hours at room temperature. After cooling to −10° C, the TAA.HCl is filtered off, and the filtrate is evaporated to dryness. The residue is dissolved in 250ml ethyl acetate and washed consecutively with water, HCl (0.05N), $D_2CO_3$ solution (5%) and NaCl solution (30%). After drying over $Na_2SO_4$, the filtrate is evaporated to dryness and the residue is crystallized from ether/petroleum ether. Yield 19.3g; melting point 108/110° C.

Rf in To:EtOH (8:2) = 0.50 on $SiO_2$.

(b). H—Ala—Ala—OMe.HCl 18.75g Boc—Ala—Ala—OMe (from (a)) is dissolved in 150ml methylene chloride, and HCl is passed into the solution for 45 minutes under constant cooling in iced water. Yield of deprotected product 14.3g. Ala—

Rf in To:EtOH (8:2) = 0.01 on $SiO_2$.

(c). Boc—Met—Ala—Ala—OMe: 15.8g Boc—Met—$N_2H_3$, dissolved in 150ml DMF, is activated at −20° C with 28.0ml 4.2N HCl in THF and 8.10ml iso-amyl nitrite. After activating for 20 minutes at −15° C, the solution is neutralized with 14.5ml NEM, after which a solution of 14.3g H—Ala—Ala—OMe.HCl (from (b)) in 75ml DMF and 1eq. NEM is added. After the pH has been adjusted to 7.2 with NEM, the reaction mixture is kept for 48 hours at about 4° C. After 48 hours, the NEM.HCl is filtered off and the filtrate is evaporated to dryness. The residue is dissolved in 300ml ethyl acetate after which it is washed with water, 0.05N HCl, 5% $NaHCO_3$ and again with water.

After drying over $Na_2SO_4$, the filtrate is evaporated to dryness and the residue is crystallized from ethyl acetate/petroleum ether (1:1) Yield 16.2g; melting point 128°–129° C.

Rf in To:EtOH (8:2) = 0.46 on $SiO_2$.

(d). Boc—Met—Ala—Ala—$N_2H_3$: 15.9g Boc—Met—Ala—Ala—OMe (from (c)) is dissolved in 160ml methanol, and 16.0ml hydrazine hydrate is added. After stirring for 3½ hours, 200ml dry ether is added. After cooling to 0° C, the solid substance is filtered off. Yield 12.6g; melting point 207°–208° C.

Rf in Am:iPro-Wa (10:4:5) = 0.41 on $SiO_2$

The following peptides are prepared in a way analogous to that indicated in I.1

| | |
|---|---|
| 2. Boc-Ala-Ala-Ala-$N_2H_3$;<br>Rf in Am:iPro:Wa (10:4:5) | = 0.44 |
| 3. Boc-Val-Ala-Ala-$N_2H_3$;<br>Rf in Am:iPro.Wa (10:4:5) | = 0.40 |
| 4. Boc-Ala-Leu-Leu-$N_2H_3$;<br>Rf in Am:iPro:Wa (10:4:5) | = 0.38 |
| 5. Boc-Met-Ala-Leu-$N_2H_3$;<br>Rf in Am:iPro:Wa (10:4:5) | = 0.39 |
| 6. Boc-Met-Val-Val-$N_2H_3$;<br>Rf in Am:iPro:Wa (10:4:5) | = 0.38 |
| 7. Boc-Met($O_2$)-Ala-Ala-$N_2H_3$;<br>Rf in Am:iPro:Wa (10:4:5) | = 0.30 |
| 8. Desamino-Met-Ala-Ala-$N_2H_{a3}$:<br>Rf in Am:iPro:Wa (10:4:5) | = 0.34 |
| 9. Desamino-Met($O_2$)-Ala-Ala-$N_2H_3$;<br>Rf in Am:iPro:Wa (10:4:5) | = 0.23 |

II C-terminal part.

1. Synthesis of H—Phe—D—Lys(Boc)—Phe—OtBu (1) Z-D-Lys(Boc)-Phe-OtBu 10.03g Z—D—Lys(Boc):ONP is dissolved in 50ml DMF and the solution, after cooling to =20° C, is added to a solution of 4.1g H—Phe—OtBu in 75ml DMF. After stirring for 1 hour at 0° C and a further 20 hours at 20° C, the reaction mixture is evaporated to dryness. The yellow residue is dissolved in ethyl acetate-water and washed with 5% potassium carbonate, water, 5% citric acid and again with water. The organic phase is dried and evaporated to dryness. The residue is dissolved in ethyl acetate and petroleum ether (40-60) is then added until the solution becomes cloudy. The resultant precipitate is subsequently filtered off.

Rf in To:EtOH (9:1) = 0.63 ($SiO_2$).

(2). H—D—Lys(Boc)—Phe—OtBu 3g of the dipeptide is dissolved in 60ml methanol. After addition of 10% palladium on charcoal, hydrogen is passed in until evolution of $CO_2$ ceases (2 hours). After filtration over hyflo, the filtrate is evaporated to dryness, resulting in a foam.

Rf in To:EtOH (9:1) = 0.21 ($SiO_2$).

(3) Z—Phe—D—Lys(Boc)—Phe—OtBu 2.18g Z—Phe—ONP is dissolved in 15ml DMF. After addition of a solution of 2.24g H—D—Lys(Boc)—Phe—OtBu (from 2) in 30ml DMF, the whole is stirred for 15 hours at 20° C.

After evaporating the yellow solution to dryness, the residue is dissolved in 15ml ethyl acetate, after which 50ml petroleum ether is added. The mixture is subsequently allowed to stand for 8 hours at 0°C, after which the precipitate formed is filtered off. Melting point 135°–138°C.

(4). H—Phe—D—Lys(Boc)—Phe—OtBu 2.5g of the tripeptide obtained in (3) is hydrogenated in the way described in (2).

Rf in To:EtOH (8:2) = 0.38 (SiO$_2$).

2.         H—Leu—D—Lys(Boc)—Phe—OtBu

5     Z—Leu—D—Lys(Boc)—Phe—OtBu

Z-Leu-ONP (3.2g) is dissolved in 40ml DMF. 3.6g H—D—Lys(Boc)—Phe—OtBu is then added to the solution, after which the mixture is stirred for 20 hours at room temperature. After evaporation of the reaction mixture to dryness, the residue is dissolved in 100ml ethyl acetate and the resultant solution is washed with 10% K$_2$CO$_3$ solution, 30% NaCl solution, citric acid solution and again with 30% NaCl solution. The ethyl acetate solution is then dried and reduced in volume by evaporation, after which petroleum ether is added to the concentrate. The precipitate formed is filtered off. Melting point 102°–105° C. Yield 4.8g.

(2). H—Leu—D—Lys(Boc)-Phe—OtBu

The tripeptide obtained in (1) is hydrogenated with Pd/C (10%) as catalyst in the way described in II.1.2

Rf in To:EtOH (8:2) = 0.41 on SiO$_2$.

3. H—Ala—D—Lys(Boc)—Phe—OtBu 2.8g Z—Ala—ONP is coupled to 3.6g H—D—Lys(-Boc)—Phe—OtBu in a way analogous to that described in 2, and the resultant protected tripeptide is then hydrogenated.

Rf in To:EtOH (8:2) = 0.37 on SiO$_2$.

4. H—Leu—D—Lys(Boc)—Tra

1. Z—Leu—D—Lys(Boc)—Tra

Z—Leu—D—Lys(Boc)—Tra is obtained in the way described in II.1.3, starting from 3.1g Z-Leu-ONP and 3g H—D—Lys(Boc)—Tra (prepared from Z—D—Lys(Boc)—Tra). Yield 65%; Rf in To:EtOH (8:2) = 0.72 on SiO$_2$.

2. H—Leu—D—Lys(Boc)—Tra 2g of the peptide (from 1) is dissolved in 25ml methanol and hydrogenated in the presence of 10% palladium on charcoal in the way described in II.1.2. Evaporation to dryness gives a foam. Yield 95%

Rf in To:EtOH (8:2) = 0.47 (SiO$_2$).

5. H—Phe—D—Lys(Boc)—Tra

Analogous to 4. Rf in To:EtCH 88:2) = 0.33

6. H—Ala—D—Lys(Boc)—Tra

Analogous to 4. Rf in To:EtOH (8:2) = 0.35

6. H—Ala—D—Lys(Boc)—Tra

Analogous to 4. Rf in To:EtOH (8:2) = 0.35

7. H—Tyr—D—Lys(Boc)—Tra

Analogous to 4. Rf in To:EtOH (8:2) = 0.24

8.          H—Leu—D—Lys(Boc)—Trp—OMe; H—Leu—D—Lys(Boc)—Trp—OH

1. Z—Leu—D—Lys(Boc)—Trp—OMe 5.57g Z—Leu—OH is dissolved in 50ml DMF, and after cooling the solution to 0° C, 3.0ml TAA and 2.0ml ethyl chloroformate are added. The reaction mixture is stirred for 15 minutes, after which 8.64g H—D—Lys(-Boc)—Trp—OMe in 50ml DMF is added at -10° C and the mixture is stirred at this temperature for 30 minutes. After stirring for a further 2 hours at 0° C and subsequently for about 5 hours at room temperature, the mixture is filtered and the filtrate is evaporated to dryness. The residue is then dissolved in ethyl acetate and the resultant solution is washed consecutively with water, 5% NaHCO$_3$ solution, water, 0.1N HCl and 30% NaCl solution.

The solution is then dried and evaporated to dryness (oil). Rf in To:EtOH (9:1) = 0.41 on SiO$_2$. Yield 10.5g.

2. Z—Leu—D—Lys(Boc)—Trp—OH

The tripeptide ester from 1. (5g) is dissolved in 100ml dioxan, after which 15.3ml 0.94N NaOH is added. The reaction mixture is stirred for 2 hours at room temperature and then acidified to pH 7 with 2N HCl. The dioxan is subsequently removed by evaporation and ethyl acetate/water is added to the residue. The mixture (aqueous layer) is then rendered acid (pH 2) without separating the layers. The organic phase is washed with 10% NaCl solution and then dried. Removal of solvent by distillation gives a foam. Rf in To:EtOH (8:2) = 0.38 on SiC$_2$. Yield 3.8g.

3. H—Leu—D—Lys(Boc)—Trp—OH 3.15g of the tripeptide obtained in 2 is dissolved in 50ml DMF and 1.67ml 4N HCl. 50mg Pd/C (10%) is then added to the solution and hydrogen is passed through for 4 hours. The catalyst is then filtered off and the filtrate is evaporated to dryness (oil). Rf in To:EtOH (9:1) = 0.10 on SiO$_2$.

4. H—Leu—D—Lys(Boc)—Trp—OMe

The peptide ester from 1 is hydrogenated in a way analogous to that described in 3., resulting in an oil. Rf in Am:Py:Wa (5:3:2) = 0.29 on SiO$_2$.

9. Preparation of H—Leu—D—Lys(Boc)—phenylalkylamides

1. Z—D—Lys(Boc)—PPA 10.33g (20.6mmol) Z-D-Lys(Boc)-ONP is dissolved in 80ml methylene chloride at about 0° C. 2.7g 3-phenylpropylamine is then added to this solution, after which the mixture is stirred for 1.5 hours at 0° C and for a further 18 hours at room temperature. The solvent is removed by evaporation and the residue is dissolved in 200 ml ethyl acetate. The ethyl acetate solution is now washed consecutively with sodium carbonate solution (10%), NaCl solution (30%), 0.1N HCl and a 30% NaCl solution, after which the ethyl acetate layer is dried and reduced by evaporation to a volume of about 80ml. Sufficient ether to cause turbidity is then added and the mixture is placed in a refrigerator. The precipitate formed is filtered off after 2 hours. Rf in Bz:EtOH (9:1) = 0.50 on SiO$_2$.

2. H—D—Lys(Boc)—PPA 8.75g of the compound obtained in 1. is dissolved in 120ml methanol to which 1.2g 10% palladium-charcoal has been added. Hydrogen is then passed through with stirring for 3.5 hours, after which the catalyst is filtered off. Evaporation of the filtrate to dryness results in an almost colourless oil, which is immediately used for further reactions. Rf in Am:Fo:Wa (7:2:1) = 0.54 SiO$_2$.

3. Z—Leu—D—Lys(Boc)—PPA 6.39g of the protected amino-acid derivative obtained in 2. is dissolved in 68ml dimethylformamide, and a solution of 7.0g Z—Leu—ONP in 20ml dimethylformamide is added. The mixture is stirred at room temperature for 20 hours, after which the solvent is removed by evaporation under vacuum. The residue is dissolved in 170ml ethyl acetate and washed consecutively with 5% potassium carbonate solution, 30% NaCl solution, 0.1N HCl and 30% NaCl solution. The ethyl acetate layer is then dried over Na$_2$SO$_4$ and evaporated to dryness. Rf in Bz:EtOH (8:2) = 0.64 on SiO$_2$.

4. H—Leu—D—Lsy(Boc)—PPA 9.0g of the peptide derivative obtained in 3. is dissolved in 300ml dimethylformamide to which 4ml 4N HCl and 1.5g 10% palladium-charcoal have been added. Hydrogen is then passed through for 3.5 hours with stirring, after which the catalyst is filtered off and the filtrate is evaporated to dryness, giving an almost colourless oil. Rf in Bu:Ac:Wa (4:1:1) = 0.55 on $SiO_2$.

5. The following are prepared in a corresponding way:
1. H—Leu—Lys(Boc)—L—Amf; Rf in To:EtOH (8:2) = 0.50 on $SiO_2$.
2. H—Leu—D—Lys(Boc)—PEA; Rf in To:EtOH (8.2) = 0.42 on $SiO_2$
3. H—Leu—D—Lys(Boc)—HPEA; Rf in To:EtOH (8:2) = 0.34 on $SiO_2$.

10. Synthesis of H—Phe—D—Lys(Boc)—Phe—Gly—OH (a) Z—Phe—D—Lys(Boc)—OMe: 29.9g Z—Phe—OH and 14.8g HOBt are dissolved in 200ml DMF. After cooling to −22° C, the following are added consecutively: a solution of 32.6g H—D—Lys(Boc)—OMe.HCl in 210ml DMF and leq.TAA, and a solution of 22.7g DCCI in 100ml DMF. The whole is then stirred for 15 minutes at −22° C, 2 hours at 0° C and about 16 hours at room temperature. After cooling, the DCHU formed is filtered off and the filtrate is evaporated to dryness. The residue is dissolved in etyl acetate and washed with water, 5% citric acid, 5% sodium bicarbonate and again with water, after which the solution is evaporated to dryness and crystallized. Yield: 51.6g; melting point: 122°-123° C. (b) Z—Phe—D—Lys(Boc)—OH: 13.7g Z—Phe—D—Lys(Boc)—OMe from (a) is dissolved in 180ml dioxan/$H_2O$ (9:1) and 15ml 2N NaOH is added. The whole is stirred for 2 hours at room temperature, after which the pH of the reaction mixture is adjusted to 7 with NHCl. The reaction mixture is subsequently reduced in volume to about 50ml (dioxan-free) and 250ml ethyl acetate is added. The mixture is washed with water and dried over $Na_2SO_4$. The $Na_2SO_4$ is filtered off and the filtrate is evaporated to dryness. The residue is crystallized from ether/petroleum ether (1:2). Yield: 11.3g; melting point 72°/75° C. Rf in To:EtOH (8:2) = 0.12 on $SiO_2$, and in Am:Py:Wa (5:3:2) = 0.69 on $SiO_2$. (c). Boc-Phe-Gly-OBzyl: leq.Nem, followed by a solution of 25.5g Boc—Phe—ONP in 100ml DMF, is added to a solution of 12.6g H—Gly—OBzl.HCl in 100ml DMF. After stirring overnight at room temperature, the reaction mixture is evaporated to dryness. The residue is dissolved in 300ml ethyl acetate/water (5:1) and washed with water.

After drying over $Na_2SO_4$, the filtrate is reduced by evaporation to a volume of about 100ml, after which 50ml petroleum ether and 250ml dry ether are added. Yield: 16.7g; melting point 126°-127° C; Rf in To:EtOH (8:2) = 0.56 on $SiO_2$. (d). H—Phe—Gly—OBZl.HCl: 8.25g Boc—Phe—Gly—OBzl is dissolved in 120ml methylene chloride and HCl gas is passed into the solution with stirring and cooling (ice/water) for 1 hour.

After 1 hour, the supply of HCl is stopped and the reaction mixture is evaporated to dryness. Yield: 6.98g of a foam-like product Rf in To:EtOH (8:2) = 0.33 on $SiO_2$. (e). Z—Phe—D—Lys(Boc)—Phe—Gly—OBzl: method analogous to the method described in (a). Reagents needed: 9.25g Z—Phe—D—Lys(Boc)—OH (from (b)), 2.92g HOBt, 6.98g H—Phe—Gly—OBzl.HCl and 4.12g DCCI. Crystallization from: ethyl acetate/petroleum ether. Yield: 12.0g; melting point 157°-159° C. Rf in To:EtOH (8:2) = 0.39 on $SiO_2$.

(f). H—Phe—D—Lys(Boc)—Phe—Gly—OH 4.11g Z—Phe—D—Lys(Boc)—Phe—Gly—OBzl is dissolved in 75ml DMF. After addition of Pd/C, hydrogen is passed in for 3 hours. The catalyst is filtered off over hyflo/asbestos and the filtrate is evaporated to dryness. Yield: 2.9g. Rf in Bu:Py:Ac:Wa (4:0.75:0.25:1) = 0.46 on $SiO_2$ The following peptides are prepared in a way analogous to that described in the previous example:

| | |
|---|---|
| 11. H-Trp-D-Lys(Boc)-Phe-Gly-OH; Rf in Bu:Py:Ac:Wa (4:0.75:0.25:1) | = 0.52 on $SiO_2$ |
| 12. H-Leu-D-Lys(Boc)-Phe-Gly-OH; Rf in Bu:Py:Ac:Wa (4:0.75:0.25:1) | = 0.40 on $SiO_2$ |
| 13. H-Val-D-Lys(Boc)-Phe-Gly-OH; Rf in Bu:Py:Ac:Wa (4:0.75:0.25:1) | = 0.42 on $SiO_2$ |
| 14. H-Ala-D-Lys(Boc)-Phe-Gly-OH; Rf in Bu:Py:Ac:Wa (4:0.75:0.25:1) | = 0.37 on $SiO_2$ |
| 15. H-Tyr-D-Lys(Boc)-Phe-Gly-OH; Rf in Bu:Py:Ac:Wa (4:0.75:0.25:1) | = 0.48 on $SiO_2$ |

EXAMPLE I

H—Met—Ala—Ala—Ala—D—Lys—Phe—Gly—OH (a). Boc—Met—Ala—Ala—Ala—D—Lys(Boc)—Phe—Gly—OH (I.1. + II.14) 1.62g Boc—Met—Ala—Ala—$N_2H_3$ is dissolved in 20ml DMF. After cooling to −20° C, 1.68ml 4.74N HCl/THF is added, followed by 0.60ml iso-amyl nitrite, and the whole is stirred for 20 minutes at −15° C, after which 0.6ml NEM is added followed by a solution of 2.3H—Ala—D—Lys(Boc)—Phe—Gly—OH in 20ml DMF, and 1.68ml 4.74N HCl/THF. The pH of the reaction mixture is adjusted to 7.2 with NEM, after which the reaction mixture is kept for 2 days at about 4° C. The NEM.HCl is then filtered off and the filtrate is evaporated to dryness. The residue is dissolved in 125ml sec.butanol/$CHCl_3$ (2:3) and 25ml $H_2O$ and the resultant solution is washed consecutively with water, 5% citric acid solution and again with water. After drying over $Na_2SO_4$, the filtrate is evaporated to dryness. The residue is dissolved in 40ml methanol to which 160ml water is then added, after which the solid substance is filtered off and dried. Yield 2.6g; Rf in Bu:Py:Ac:Wa (4:0.75:0.25:1) = 0.62 on $SiO_2$; Melting point 202°-203° (dec.)

(b). H—Met—Ala—Ala—Ala—D—Lys—Phe—Gly—OH.acetate 2.6 g of the peptide obtained in a. is dissolved in 26ml 90% TFA. After stirring for 45 minutes at room temperature under a nitrogen atmosphere, the solution is added dropwise to 250ml dry ether. The precipitate formed is filtered off and dried, after which the solid substance is dissolved in 40ml tert.butanol/water (1:1) and the resultant solution is stirred with an ion exchange resin in acetate form. After stirring for 30 minutes, the ion exchange resin is filtered off and the filtrate is evaporated to dryness. The residue is then subjected to purification by means of counter current distribution; yield 78%. Rf in Bu:Py:Ac:Wa (4:0.75:0.25:1) = 0.25 on $SiO_2$.

EXAMPLE II

The following peptides are prepared as their acetate salts in a way corresponding to that described in Example I:

| | |
|---|---|
| 1. H-Met-Ala-Ala-Phe-D-Lys-Phe-Gly-OH Rf = 0.24 | (I.1 + II.10) |
| 2. H-Met-Ala-Trp-D-Lys-Phe-Gly-OH | (I.1 + II.11) |

-continued

| | | |
|---|---|---|
| | Rf = 0.27 | |
| 3. | H-Met-Ala-Ala-Leu-D-Lys-Phe-Gly-OH Rf = 0.22 | (I.1 + II.12) |
| 4. | H-Met-Ala-Ala-Val-D-Lys-Phe-Gly-OH Rf = 0.18 | (I.1 + II.13) |
| 5. | H-Met-Ala-Ala-Tyr-D-Lys-Phe-Gly-OH Rf = 0.23 | (I.1 + II.15) |
| 6. | H-Ala-Ala-Ala-Phe-D-Lys-Phe-Gly-OH Rf = 0.21 | (I.2 + II.10) |
| 7. | H-Val-Ala-Ala-Phe-D-Lys-Phe-Gly-OH Rf = 0.26 | (I.3 + II.10) |
| 8. | H-Ala-Ala-Ala-Ala-D-Lys-Phe-Gly-OH Rf = 0.20 | (I.2 + II.14) |
| 9. | H-Ala-Leu-Leu-Leu-D-Lys-Phe-Gly-OH Rf = 0.19 | (I.4 + II.12) |
| 10. | H-Met-Ala-Leu-Phe-D-Lys-Phe-Gly-OH Rf = 0.18 | (I.5 + II.10) |
| 11. | H-Met-Val-Val-Phe-D-Lys-Phe-Gly-OH Rf = 0.22 | (I.6 + II.10) |
| 12. | H-Met($O_2$)-Ala-Ala-Phe-D-Lys-Phe Gly-OH Rf = 0.16 | (I.7 + II.10) |
| 13. | desamino-Met-Ala-Ala-Phe-D-Lys-Phe-Gly-OH Rf = 0.36 | (I.8 + II.10) |
| 14. | desamino-Met($O_2$)-Ala-Ala-Phe-D-Lys-Phe-Gly-OH Rf = 0.28 | |

EXAMPLE III

The following peptides are prepared as their acetate salts in a way corresponding to that described in Example I:

| | | |
|---|---|---|
| 1. | H-Met-Ala-Ala-Phe-D-Lys-Phe-OH Rf = 0.27 | (I.1 + II.1) |
| 2. | H-Met-Ala-Ala-Leu-D-Lys-Phe-OH Rf = 0.28 | (I.1 + II.2) |
| 3. | H-Met($O_2$)-Ala-Ala-Ala-D-Lys-Phe-OH Rf = 0.18 | (I.7 + II.3) |
| 4. | H-Met($O_2$)-Ala-Ala-Leu-D-Lys-Tra Rf = 0.11 | (I.7 + II.4) |
| 5. | desamino-Met-Ala-Ala-Phe-D-Lys-Tra Rf = 0.14 | (I.8 + II.5) |
| 6. | desamino-Met($O_2$)-Ala-Ala-Ala-D-Lys-Tra Rf = 0.18 | (I.9 + II.6) |
| 7. | H-Met-Ala-Leu-Tyr-D-Lys-Tra Rf = 0.17 | (I.5 + II.7) |
| 8. | H-Met-Ala-Ala-Leu-D-Lys-Trp-OMe Rf 0.31 | (I.1 + II.8) |
| 9. | H-Met-Ala-Ala-Leu-D-Lys-Trp-OH Rf = 0.18 | (I.1 + II.8.3) |
| 10. | H-Met-Ala-Ala-Leu-D-Lys-PPA Rf = 0.22 | (I.1 + II.9.4) |
| 11. | H-Met-Ala-Ala-Leu-D-Lys-L-Amf Rf = 0.24 | (I.1 + II.9.5.1) |
| 12. | H-Met-Ala-Ala-Leu-D-Lys-PEA Rf = 0.21 | (I.1 + II.9.5.2) |
| 13. | H-Met-Ala-Ala-Leu-D-Lys-HPEA Rf = 0.26 | (I.1 + II.9.5.3) |
| 14. | H-Met($O_2$)-Ala-Ala-Phe-D-Lys-Phe-OH Rf = 0.19 | (I.7 + II.1) |
| 15. | H-Ala-Leu-Phe-D-Lys-Phe-OH Rf = 0.32 | (I.4 + II.1) |
| 16. | desamino-Met-Ala-Ala-Phe-D-Lys-Phe-OH Rf = 0.35 | (I.8 + II.1) |

Unless otherwise indicated, the Rf values given in examples II and III are for the eluent Bu:Py:Ac:Wa (4:0.75:0.25:1) on $SiO_2$.

EXAMPLE IV

Sulphoxides 0.06mmol of the peptide is dissolved in 5ml acetic acid and 15μl 30% hydrogen peroxide is added to the solution, which is then stirred for 1 hour at room temperature. A suspension of 20mg platinum black in 2.5ml glacial acetic acid is then added. The mixture is stirred for 30 minutes, after which it is filtered. The filtrate is evaporated to dryness under vacuum and the residue is added to 10ml tert-butanol/water. The mixture is then lyophilized. The acetates of the following peptides are prepared in this way:

| | |
|---|---|
| 1. | H-Met(O)-Ala-Ala-Ala-D-Lys-Phe-Gly-OH Rf = 0.12 |
| 2. | H-Met(O)-Ala-Ala-Phe-D-Lys-Phe-Gly-OH Rf = 0.10 |
| 3. | H-Met(O)-Ala-Leu-Phe-D-Lys-Phe-Gly-OH Rf = 0.11 |
| 4. | desamino-Met(O)-Ala-Ala-Phe-D-Lys-Phe-Gly-OH Rf = 0.26 |
| 5. | H-Met(O)-Ala-Ala-Phe-D-Lys-Phe-OH Rf = 0.13 |
| 6. | desamino-Met(O)-Ala-Ala-Phe-D-Lys-Tra Rf = 0.15 |
| 7. | H-Met(O)-Ala-Ala-Leu-D-Lys-PPA Rf = 0.08 |
| 8. | desamino-Met(O)-Ala-Ala-Phe-D-Lys-Phe-OH Rf = 0.19 |
| 9. | H-Met(O)-Ala-Ala-Leu-D-Lys-Trp-OMe Rf = 0.21 |

The Rf values given are for Bu:Py:Ac:Wa (4:0.75:0.25:1) on $SiO_2$

EXAMPLE V

Sulphones 0.2mmol of the peptide is dissolved in a mixture of 0.5ml water, 0.1ml 4N perchloric acid and 0.02ml 0.5M ammonium molybdate, after which 0.06ml 30% hydrogen peroxide is added to this mixture. The mixture is stirred for 2 hours at a temperature of about 10° C, after which it is diluted with 25ml tert. butanol/water. An ion exchange resin (Dowex X-8 in acetate form) is then added to the mixture, which is stirred for 30 minutes. The mixture is subsequently filtered and the filtrate lyophilized.

The following acetates are prepared in this way:

| | |
|---|---|
| 1. | H-Met($O_2$)-Ala-Ala-Phe-D-Lys-Phe-Gly-OH Rf = 0.18 |
| 2. | H-Met($O_2$)-Ala-Ala-Phe-D-Lys-Phe-OH Rf = 0.20 |
| 3. | desamino-Met($O_2$)-Ala-Ala-Phe-D-Lys-Phe-OH Rf = 0.23 |

The Rf values given are for Bu:Py:Ac:Wa (4:0.75:0.25:1) on $SiO_2$.

EXAMPLE VI

Zinc complexes 1.5ml of a solution of zinc chloride, containing 50mg zinc per ml, is added to a solution of 31.5mg $Na_2HPO_4.2H_2O$ in 30ml distilled water. The precipitate of zinc phosphate thus formed is redissolved by the addition of 4N HCl, after which 175mg NaCl and 0.5g benzyl alcohol are added to the mixture. 1.5mg of the hexapeptide H—Met—Ala—Ala—Phe—D—Lys—Phe—OH (example III.1) is then dissolved in this mixture and sufficient N sodium hydroxide is subsequently added to adjust the pH of the mixture to 8.5. The volume is then made up to 50 ml with distilled water.

| 1 ml suspension contains | 30 μg hexapeptide |
|---|---|
| | 1.5 mg zinc |
| | 0.63 mg $Na_2HPO_4.2H_2O$ |
| | 3.5 mg NaCl |
| | 10 mg benzyl alcohol |

EXAMPLE VII

Injection preparation
peptide of example I — 1.5 mg
NaCl — 9.0mg methyloxy-benzoate — 1.2mg
distilled, pyrogen free water — 1.0 ml

EXAMPLE VIII

Capsule
Hard shell gelatin capsule containing:
peptide of example III.14 (= Ex. V.2) — 2.5 mg
magnesium stearate — 1.4 mg
povidone — 5.5 mg
mannitol — 137.0 mg

We claim:

1. Compound of the formula:

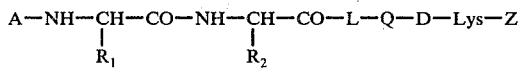

and their functional derivatives, wherein:

A is an N-terminal chain prolongation selected from the group consisting of H-(L or D)Met, H-(L or D) Met(→O), H-(L or D)Met(→O$_2$), desamino-Met, desaminoMet(→O), desamino-Met(→O$_2$), and H N-B-CO-, wherein B represents a branched or straight-chain alkylene (C$_1$-C$_6$) or alkylidene (C$_1$-C$_6$) group;

Q is an amino-acid residue -NH-CHR-CO-, wherein R is selected from the group consisting of alkyl (C$_1$-C$_6$), p-hydroxyphenylmethyl, 3-indolymethyl, and phenylemethyl radicals;

R$_1$ and R$_2$ each selected from hydrogen and alkyl (1-6C) groups; and

Z is selected from the group consisting of N-(phenylalkyl)amino, N-(B-indolylalkyl)amino, L-Trp, L-Phe-OH, L-Trp-Gly-OH, and L-Phe-Gly-OH.

2. A compound as recited in claim 1, wherein Q represents Phe or Ala.

3. A compound as recited in claim 1, wherein A represents L-Met, L-Met(→O), L-Met(→O$_2$), desamino-Met, desamino-Met(→O), or desamino-Met(→O$_2$).

4. A compound as recited in claim 1, wherein R$_1$ and R$_2$ are both methyl.

5. A compound as recited in claim 1, in which Z is Phe-OH.

6. A compound as recited in claim 5, in which A is L-Met(→O$_2$), Q is Phe and R$_1$ and R$_2$ are both methyl.

7. A compound as recited in claim 5, in which A is L-Met(→O$_2$), Q is Ala, and R$_1$ and R$_2$ are both methyl.

8. A pharmaceutical composition having conditioned flight inhibiting psychopharmacological properties, comprising:

(A) a pharmaceutically effective amount of a compound of the formula:

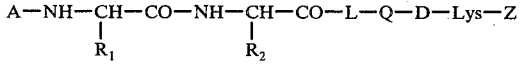

or a functional derivative thereof, wherein:

A is an N-terminal chain prolongation selected from the group consisting of H—(L or D)Met, H—(L or D) Met(→O), H—(L or D)Met(→O$_2$), desamino-Met, desamino-Met(→O), desamino-Met(→0$_2$), and H$_2$N—B—CO—, wherein B represents a branched or straight-chain alkylene (C$_1$-C$_6$) or alkylidene (C$_1$-C$_6$) group;

Q is an amino-acid residue —NH—CHR—CO—, wherein R is selected from the group consisting of alkyl (C$_1$-C$_6$), p-hydroxyphenylmethyl, 3-idolylmethyl, and phenylmethyl radials;

R$_1$ and R$_2$ each selected from hydrogen and alkyl (1-6C) groups; and

Z is seleted from the group consisting of N-(phenylalkyl)amino, N-($\beta$-indolylalkyl)amino, L-Trp, L-Phe-OH, L-Trp-Gly-OH, and L-Phe-Gly-OH; and (B) a pharmaceutically acceptable carrier therefor.

9. A composition as recited in claim 8 wherein Q represents Phe or Ala.

10. A composition as recited in claim 8, wherein A represents L-met, L-Met(→O), L-Met(→O$_2$), desamino-Met, desamino Met(→O), or desamino-Met(→O$_2$).

11. A composition as recited in claim 8, wherein R$_1$ and R$_2$ are both methyl.

12. A composition as recited in claim 8 wherein Z is Phe-OH.

13. A composition as recited in claim 12 wherein A is L-Met(→O$_2$), Q is Phe and R$_1$ and R$_2$ are both methyl.

14. A composition as recited in claim 12 wherein A is L-Met(→O$_2$), Q is Ala and R$_1$ and R$_2$ are both methyl.

15. The compound: H—L—Met—L—Ala—L—Ala—L—Phe—O—Lys—L—Phe—OH.

16. The compound: H—L—Met-(O)—L—Ala—L—Ala—L—Phe—D—Lys—L—Phe—OH.

17. The compound: H—L—Met(O$_2$)—L—Ala—L—Ala—L—Phe—D—Lys—L—Phe—OH.

18. The compound: H—Met—L—Ala—L—Ala—L—Ala—D—Lys—L—Phe—Gly—Oh.

19. The compound: H—L—Met-(O)—L—Ala—L—Ala—L—Ala—D—Lys—L—Phe—Gly—OH.

20. The compound: H—L—Met(O$_2$)—L—Ala—L—Ala—L—Ala—D—Lys—L—Phe—OH.

21. The compound: desamino-Met—L—Ala—L—Ala—L—Phe—D—Lys—L—Phe—OH.

22. The compound: desamino-Met(O$_2$)—L—Ala—L—Ala—L—Phe—D—Lys—L—Phe—Oh.

23. The compound: desamino-Met-(O)—Ala—L—Ala—L—Phe—D—Lys—L—Phe—Gly—OH.

* * * * *